(12) United States Patent
Dugan et al.

(10) Patent No.: US 8,454,437 B2
(45) Date of Patent: Jun. 4, 2013

(54) SYSTEMS AND METHODS FOR PORTABLE EXERGAMING

(76) Inventors: Brian M. Dugan, Sleepy Hollow, NY (US); Steven M. Santisi, Ridgefield, CT (US); Jean Pierre Latrille, Sleepy Hollow, NY (US); Lieven Nuyttens, Larchmont, NY (US)

( * ) Notice: Subject to any disclaimer, the term of this patent is extended or adjusted under 35 U.S.C. 154(b) by 179 days.

(21) Appl. No.: 12/839,098

(22) Filed: Jul. 19, 2010

(65) Prior Publication Data

US 2011/0065504 A1    Mar. 17, 2011

Related U.S. Application Data

(60) Provisional application No. 61/226,624, filed on Jul. 17, 2009.

(51) Int. Cl.
*A63F 9/24* (2006.01)
(52) U.S. Cl.
USPC .................................. 463/31; 463/22; 463/36
(58) Field of Classification Search
USPC ................................................ 463/31, 22, 36
See application file for complete search history.

(56) References Cited

U.S. PATENT DOCUMENTS

| | | |
|---|---|---|
| 3,717,857 A | 2/1973 | Evans |
| 3,788,647 A | 1/1974 | Evans |
| 3,815,427 A | 6/1974 | Gladstone |
| 3,834,702 A | 9/1974 | Bliss |
| 4,484,743 A | 11/1984 | Williams |
| 4,542,897 A | 9/1985 | Melton et al. |
| 4,735,410 A | 4/1988 | Nobuta |
| 4,817,938 A | 4/1989 | Nakao et al. |
| 4,858,930 A | 8/1989 | Sato |
| 4,976,435 A | 12/1990 | Shatford et al. |
| 5,001,632 A | 3/1991 | Hall-Tipping |
| 5,056,783 A | 10/1991 | Matcovich et al. |
| 5,174,577 A | 12/1992 | Warde et al. |
| 5,221,088 A | 6/1993 | McTeigue et al. |
| 5,233,544 A | 8/1993 | Kobayashi |

(Continued)

FOREIGN PATENT DOCUMENTS

| | | |
|---|---|---|
| EP | 0 753 836 A2 | 1/1997 |
| EP | 1 292 217 B1 | 11/2005 |

(Continued)

OTHER PUBLICATIONS

Nov. 10, 2009 Response to Office Action of U.S. Appl. No. 11/676,666 mailed Jun. 10, 2009.

(Continued)

*Primary Examiner* — Pierre E Elisca
(74) *Attorney, Agent, or Firm* — Dugan & Dugan, PC

(57) ABSTRACT

In a first aspect, a system for playing a video game is provided that includes (1) one or more sensors adapted to monitor one or more biometric parameters of a user and communicate the one or more monitored biometric parameters (MBPs); (2) a computing device adapted to communicate with the one or more sensors and to receive the one or more communicated MBPs; and (3) a video game having an avatar adapted to move an object on an incline, the video game adapted to execute on the computing device. The video game is adapted to control the avatar to perform an action in the video game based in part on the received one or more communicated MBPs. Numerous other aspects are provided.

23 Claims, 3 Drawing Sheets

U.S. PATENT DOCUMENTS

| | | |
|---|---|---|
| 5,257,084 A | 10/1993 | Marsh |
| RE34,728 E | 9/1994 | Hall-Tipping |
| 5,362,069 A | 11/1994 | Hall-Tipping |
| 5,377,100 A | 12/1994 | Pope et al. |
| 5,462,504 A | 10/1995 | Trulaske et al. |
| 5,515,865 A | 5/1996 | Scanlon |
| 5,527,239 A | 6/1996 | Abbondanza |
| 5,591,104 A | 1/1997 | Andrus et al. |
| 5,592,401 A | 1/1997 | Kramer |
| 5,624,316 A | 4/1997 | Roskowski et al. |
| 5,645,513 A | 7/1997 | Haydocy et al. |
| 5,667,459 A | 9/1997 | Su |
| 5,672,107 A | 9/1997 | Clayman |
| 5,673,691 A | 10/1997 | Abrams et al. |
| 5,688,183 A | 11/1997 | Sabatino et al. |
| 5,694,340 A | 12/1997 | Kim |
| 5,702,323 A | 12/1997 | Poulton |
| 5,741,182 A | 4/1998 | Lipps et al. |
| 5,781,698 A | 7/1998 | Teller et al. |
| 5,884,281 A | 3/1999 | Smith et al. |
| 5,885,156 A | 3/1999 | Toyohara et al. |
| 5,911,635 A | 6/1999 | Ogden |
| 5,918,603 A | 7/1999 | Brown |
| 5,928,133 A | 7/1999 | Halyak |
| 5,947,868 A | 9/1999 | Dugan |
| 5,954,510 A | 9/1999 | Merrill et al. |
| 6,024,675 A | 2/2000 | Kashiwaguchi |
| 6,038,546 A | 3/2000 | Ferro |
| 6,045,364 A | 4/2000 | Dugan |
| 6,062,216 A | 5/2000 | Corn |
| 6,152,856 A | 11/2000 | Studor et al. |
| 6,173,610 B1 | 1/2001 | Pace |
| 6,179,713 B1 | 1/2001 | James et al. |
| D439,981 S | 4/2001 | Kasabach et al. |
| 6,213,872 B1 | 4/2001 | Harada et al. |
| 6,244,988 B1 | 6/2001 | Delman |
| 6,251,010 B1 | 6/2001 | Tajiri et al. |
| 6,261,102 B1 | 7/2001 | Dugan et al. |
| 6,267,677 B1 | 7/2001 | Tajiri et al. |
| 6,302,789 B2 | 10/2001 | Harada et al. |
| D451,604 S | 12/2001 | Kasabach et al. |
| 6,347,993 B1 | 2/2002 | Kondo et al. |
| 6,354,940 B1 | 3/2002 | Itou et al. |
| 6,375,572 B1 | 4/2002 | Masuyama et al. |
| D460,971 S | 7/2002 | Sica et al. |
| 6,456,749 B1 | 9/2002 | Kasabach et al. |
| 6,478,736 B1 | 11/2002 | Mault |
| 6,482,092 B1 | 11/2002 | Tajiri et al. |
| 6,494,830 B1 | 12/2002 | Wessel |
| 6,513,017 B1 | 1/2003 | Howard et al. |
| 6,513,160 B2 | 1/2003 | Dureau |
| 6,514,199 B1 | 2/2003 | Alessandri |
| 6,527,711 B1 | 3/2003 | Stivoric et al. |
| 6,553,386 B1 | 4/2003 | Alabaster |
| 6,559,620 B2 | 5/2003 | Zhou et al. |
| 6,579,231 B1 | 6/2003 | Phipps |
| 6,595,858 B1 | 7/2003 | Tajiri et al. |
| 6,595,929 B2 | 7/2003 | Stivoric et al. |
| 6,605,038 B1 | 8/2003 | Teller et al. |
| 6,628,847 B1 | 9/2003 | Kasabach et al. |
| 6,641,482 B2 | 11/2003 | Masuyama et al. |
| 6,652,383 B1 | 11/2003 | Sonoda et al. |
| 6,705,972 B1 | 3/2004 | Takano et al. |
| 6,720,983 B1 | 4/2004 | Massaro et al. |
| 6,746,371 B1 | 6/2004 | Brown et al. |
| 6,758,746 B1 | 7/2004 | Hunter et al. |
| 6,786,825 B2 | 9/2004 | Kawazu |
| 6,790,178 B1 | 9/2004 | Mault et al. |
| 6,796,927 B2 | 9/2004 | Toyama |
| 6,811,516 B1 | 11/2004 | Dugan |
| 6,881,176 B2 | 4/2005 | Oishi et al. |
| 6,888,779 B2 | 5/2005 | Mollicone et al. |
| 6,902,513 B1 | 6/2005 | McClure |
| 6,966,837 B1 | 11/2005 | Best |
| 6,974,078 B1 | 12/2005 | Simon |
| 7,020,508 B2 | 3/2006 | Stivoric et al. |
| 7,021,140 B2 | 4/2006 | Perkins |
| 7,041,049 B1 | 5/2006 | Raniere |
| 7,057,551 B1 | 6/2006 | Vogt |
| 7,068,860 B2 | 6/2006 | Kasabach et al. |
| 7,153,262 B2 | 12/2006 | Stivoric et al. |
| 7,189,191 B2 | 3/2007 | Dugan |
| 7,261,690 B2 | 8/2007 | Teller et al. |
| 7,285,090 B2 | 10/2007 | Stivoric et al. |
| 7,931,563 B2 | 4/2011 | Shaw et al. |
| 8,188,868 B2 | 5/2012 | Case, Jr. |
| 2002/0022516 A1 | 2/2002 | Forden |
| 2002/0082065 A1 | 6/2002 | Fogel et al. |
| 2002/0082077 A1 | 6/2002 | Johnson et al. |
| 2002/0090985 A1 | 7/2002 | Tochner et al. |
| 2002/0107433 A1 | 8/2002 | Mault |
| 2002/0151992 A1* | 10/2002 | Hoffberg et al. ............... 700/83 |
| 2002/0160883 A1 | 10/2002 | Dugan |
| 2002/0163495 A1 | 11/2002 | Doynov |
| 2003/0149344 A1 | 8/2003 | Nizan |
| 2004/0023761 A1 | 2/2004 | Emery |
| 2004/0053690 A1 | 3/2004 | Fogel et al. |
| 2005/0032525 A1 | 2/2005 | Gasbarro |
| 2005/0068169 A1 | 3/2005 | Copley et al. |
| 2005/0101845 A1 | 5/2005 | Nihtila |
| 2005/0177051 A1 | 8/2005 | Almen |
| 2005/0215340 A1 | 9/2005 | Stites et al. |
| 2005/0288119 A1 | 12/2005 | Wang et al. |
| 2006/0025229 A1 | 2/2006 | Mahajan et al. |
| 2006/0025282 A1 | 2/2006 | Redmann |
| 2006/0031102 A1 | 2/2006 | Teller et al. |
| 2006/0122474 A1 | 6/2006 | Teller et al. |
| 2006/0224051 A1 | 10/2006 | Teller et al. |
| 2006/0264730 A1 | 11/2006 | Stivoric et al. |
| 2006/0281543 A1* | 12/2006 | Sutton et al. ................ 463/29 |
| 2007/0038038 A1 | 2/2007 | Stivoric et al. |
| 2007/0053513 A1* | 3/2007 | Hoffberg ................... 380/201 |
| 2007/0109491 A1 | 5/2007 | Howell et al. |
| 2007/0111811 A1 | 5/2007 | Grober |
| 2007/0111858 A1 | 5/2007 | Dugan |
| 2007/0135266 A1 | 6/2007 | Dugan |
| 2007/0167204 A1 | 7/2007 | Lyle et al. |
| 2007/0197274 A1 | 8/2007 | Dugan |
| 2007/0208233 A1 | 9/2007 | Kovacs |
| 2007/0260482 A1 | 11/2007 | Nurmela et al. |
| 2008/0027337 A1 | 1/2008 | Dugan et al. |
| 2008/0085778 A1 | 4/2008 | Dugan |
| 2008/0094226 A1 | 4/2008 | O'Shea et al. |
| 2008/0129518 A1 | 6/2008 | Carlton-Foss |
| 2008/0146892 A1 | 6/2008 | LeBoeuf et al. |
| 2008/0167861 A1 | 7/2008 | Inoue et al. |
| 2008/0191864 A1 | 8/2008 | Wolfson |
| 2008/0218310 A1 | 9/2008 | Alten et al. |
| 2008/0281633 A1 | 11/2008 | Burdea et al. |
| 2008/0318679 A1 | 12/2008 | Tran et al. |
| 2009/0121894 A1 | 5/2009 | Wilson et al. |
| 2009/0270743 A1 | 10/2009 | Dugan et al. |
| 2010/0033303 A1 | 2/2010 | Dugan et al. |
| 2010/0130298 A1 | 5/2010 | Dugan et al. |
| 2010/0160041 A1* | 6/2010 | Grant et al. ................ 463/31 |
| 2010/0240458 A1* | 9/2010 | Gaiba et al. ............... 463/36 |
| 2011/0190055 A1* | 8/2011 | Leyvand et al. ........... 463/36 |
| 2011/0260830 A1* | 10/2011 | Weising ................. 340/5.52 |

FOREIGN PATENT DOCUMENTS

| | | |
|---|---|---|
| EP | 1 639 939 A1 | 3/2006 |
| EP | 1 292 218 B1 | 4/2006 |
| EP | 1 702 560 A1 | 9/2006 |
| EP | 1 743 571 A2 | 1/2007 |
| JP | 58044078 | 3/1983 |
| JP | 58 195577 | 11/1983 |
| JP | 58 195578 | 11/1983 |
| JP | 08103568 | 4/1996 |
| WO | WO 94/17860 | 8/1994 |
| WO | WO 96/05766 A1 | 2/1996 |
| WO | WO 97/02550 | 1/1997 |
| WO | WO 01/96986 A2 | 12/2001 |
| WO | WO 02/00111 A1 | 1/2002 |
| WO | WO 02/078538 A2 | 10/2002 |
| WO | WO 03/015005 A2 | 2/2003 |
| WO | WO 2004/019172 A2 | 3/2004 |
| WO | WO 2004/032715 A2 | 4/2004 |

| WO | WO 2004/034221 A2 | 4/2004 |
| WO | WO 2005/016124 A2 | 2/2005 |
| WO | WO 2005/027720 A2 | 3/2005 |
| WO | WO 2005/029242 A2 | 3/2005 |
| WO | WO 2005/092177 A1 | 10/2005 |

OTHER PUBLICATIONS

Office Action of U.S. Appl. No. 11/620,046 Mailed Nov. 12, 2009.
Office Action of U.S. Appl. No. 11/869,695 Mailed Nov. 17, 2009.
Dec. 21, 2009 Response to Office Action of U.S. Appl. No. 11/768,167 mailed Aug. 19, 2009.
Jan. 7, 2010 Response to Office Action of U.S. Appl. No. 11/692,185 mailed Oct. 7, 2009.
Feb. 12, 2010 Response to Office Action of U.S. Appl. No. 11/620,046 Mailed Nov. 12, 2009.
Final Office Action of U.S. Appl. No. 11/676,666 mailed Feb. 5, 2010.
Feb. 17, 2010 Response to Office Action of U.S. Appl. No. 11/869,695 Mailed Nov. 17, 2009.
Final Office Action of U.S. Appl. No. 11/692,185 mailed Mar. 3, 2010.
Final Office Action of U.S. Appl. No. 11/768,167 mailed Mar. 24, 2010.
Office Action of U.S. Appl. No. 10/094,396 mailed Apr. 14, 2010.
May 5, 2010 Response to Final Office Action of U.S. Appl. No. 11/676,666 mailed Feb. 5, 2010.
Final Office Action of U.S. Appl. No. 11/869,695 Mailed May 26, 2010.
Appeal Brief of U.S. Appl. No. 11/692,185 mailed Jun. 3, 2010.
Jun. 24, 2010 Response to Final Office Action of U.S. Appl. No. 11/768,167 mailed Mar. 24, 2010.
Final Office Action of U.S. Appl. No. 11/620,046 Mailed Jun. 23, 2010.
Advisory Action of U.S. Appl. No. 11/768,167 mailed Jun. 30, 2010.
Interview Summary of U.S. Appl. No. 11/676,666 filed Jul. 9, 2010.
Jul. 14, 2010 Response to Office Action of U.S. Appl. No. 10/094,396 mailed Apr. 14, 2010.
Advisory Action of U.S. Appl. No. 11/676,666 mailed Jul. 12, 2010.
Amendment submitted with RCE of U.S. Appl. No. 11/676,666 filed Aug. 5, 2010.
Examiner Interview Summary of U.S. Appl. No. 11/676,666 mailed Aug. 5, 2010.
Interview Summary of U.S. Appl. No. 11/676,666 filed Aug. 11, 2010.
Interview Summary of U.S. Appl. No. 11/869,695 filed Feb. 3, 2010.
Interview Summary of U.S. Appl. No. 11/869,695 filed Feb. 17, 2010.
Restriction Requirement of U.S. Appl. No. 10/945,808 mailed Aug. 22, 2005.
Sep. 22, 2005 Response to Restriction Requirement of U.S. Appl. No. 10/945,808 mailed Aug. 22, 2005.
Restriction Requirement of U.S. Appl. No. 10/945,808 mailed Jan. 10, 2006.
Feb. 10, 2006 Response to Restriction Requirement of U.S. Appl. No. 10/945,808 mailed Jan. 10, 2006.
Restriction Requirement of U.S. Appl. No. 10/094,396 mailed May 4, 2004.
Jul. 2, 2004 Response to Restriction Requirement of U.S. Appl. No. 10/094,396 mailed May 4, 2004.
Interview Summary of U.S. Appl. No. 10/094,396 filed Nov. 7, 2005.
Restriction Requirement of U.S. Appl. No. 10/094,396 mailed Oct. 31, 2006.
Jan. 31, 2007 Response to Restriction Requirement of U.S. Appl. No. 10/094,396 mailed Oct. 31, 2006.
Restriction Requirement of U.S. Appl. No. 11/620,046 Mailed Jun. 23, 2009.
Jul. 24, 2009 Response to Restriction Requirement of U.S. Appl. No. 11/620,046 Mailed Jun. 23, 2009.
Examiner Interview Summary of U.S. Appl. No. 11/692,185 mailed Jan. 15, 2010.
Interview Summary of U.S. Appl. No. 11/692,185 filed Jan. 26, 2010.
Interview Summary of U.S. Appl. No. 11/692,185 filed Feb. 3, 2010.
Notice of Allowance of U.S. Appl. No. 11/676,666 mailed Aug. 19, 2010.
Amendment After Final submitted with RCE of U.S. Appl. No. 11/869,695 filed Aug. 26, 2010.
Examiner Answer of U.S. Appl. No. 11/692,185 mailed Sep. 22, 2010.
Final Office Action of U.S. Appl. No. 10/094,396 mailed Oct. 14, 2010.
Office Action of U.S. Appl. No. 11/869,695 mailed Oct. 18, 2010.
Office Action of U.S. Appl. No. 12/696,040 mailed Jun. 8, 2011.
May 27, 2011 Response to Office Action of U.S. Appl. No. 11/768,167 mailed Dec. 27, 2010.
Final Office Action of U.S. Appl. No. 11/869,695 mailed Jun. 21, 2011.
Dugan, U.S. Appl. No. 13/183,405, filed Jul. 14, 2011.
Mar. 18, 2011 Response to Office Action of U.S. Appl. No. 11/869,695 mailed Oct. 18, 2010.
Office Action of U.S. Appl. No. 12/979,275 mailed Mar. 7, 2011.
Tom Foremski, Key Centre for Developing New Internet Devices, Financial Times, Survey London Edition 1 ED, p. 12, Oct. 2, 1996.
Busch, Fritz "Diabetes Institute Brings Dakota, New Ulm Together" Jun. 10, 2001. Ogden Newspapers, Inc.
"Bluetooth." Wikipedia: The Free Encyclopedia. Aug. 10, 2009 <http://en.wikipedia.org/wiki/Bluetooth>.
Notice of Allowance of U.S. Appl. No. 08/858,824 mailed Sep. 1, 1998.
Notice of Abandonment of U.S. Appl. No. 08/858,824 mailed Feb. 3, 1999.
Withdrawal of Notice of Allowance of U.S. Appl. No. 08/858,824 mailed May 11, 1999.
Notice of Allowance of U.S. Appl. No. 08/858,824 mailed Jul. 30, 1999.
Office Action of U.S. Appl. No. 09/104,917 mailed Sep. 22, 1998.
Dec. 22, 1998 Response to Office Action of U.S. Appl. No. 09/104,917 mailed Sep. 22, 1998.
Notice of Allowance of U.S. Appl. No. 09/104,917 mailed Mar. 15, 1999.
Office Action of U.S. Appl. No. 09/702,179 mailed Sep. 29, 2003.
Mar. 29, 2004 Response to Office Action of U.S. Appl. No. 09/702,179 mailed Sep. 29, 2003.
Notice of Allowance of U.S. Appl. No. 09/702,179 mailed Jun. 21, 2004.
Preliminary Amendment of U.S. Appl. No. 10/945,808 mailed Jul. 11, 2005.
Office Action of U.S. Appl. No. 10/945,808 mailed Apr. 14, 2006.
Sep. 14, 2006 Response to Office Action of U.S. Appl. No. 10/945,808 mailed Apr. 14, 2006.
Notice of Allowance of U.S. Appl. No. 10/945,808 mailed Nov. 3, 2006.
Office Action of U.S. Appl. No. 11/676,666 mailed Sep. 18, 2008.
Feb. 18, 2009 Response to Office Action of U.S. Appl. No. 11/676,666 mailed Sep. 18, 2008.
Office Action of U.S. Appl. No. 11/676,666 mailed Jun. 10, 2009.
Preliminary Amendment of U.S. Appl. No. 10/094,396 mailed May 20, 2002.
Office Action of U.S. Appl. No. 10/094,396 mailed Oct. 4, 2004.
Mar. 4, 2005 Response to Office Action of U.S. Appl. No. 10/094,396 mailed Oct. 4, 2004.
Final Office Action of U.S. Appl. No. 10/094,396 mailed Jun. 2, 2005.
Nov. 2, 2005 Response to Final Office Action of U.S. Appl. No. 10/094,396 mailed Jun. 2, 2005.
Office Action of U.S. Appl. No. 10/094,396 mailed Feb. 9, 2006.
Aug. 9, 2006 Response to Office Action of U.S. Appl. No. 10/094,396 mailed Feb. 9, 2006.
Office Action of U.S. Appl. No. 10/094,396 mailed May 4, 2007.
Oct. 4, 2007 Response to Office Action of U.S. Appl. No. 10/094,396 mailed May 4, 2007.
Office Action of U.S. Appl. No. 10/094,396 mailed Jan. 25, 2008.
Jul. 25, 2008 Response to Office Action of U.S. Appl. No. 10/094,396 mailed Jan. 25, 2008.
Final Office Action of U.S. Appl. No. 10/094,396 mailed May 13, 2009.
Office Action of U.S. Appl. No. 11/692,185 mailed Oct. 7, 2009.

Notice of Non-Compliant Response of U.S. Appl. No. 11/768,167 mailed May 6, 2009.
Jun. 8, 2009 Response to Notice of Non-Compliant Response of U.S. Appl. No. 11/768,167 mailed May 6, 2009.
Office Action of U.S. Appl. No. 11/768,167 mailed Aug. 19, 2009.
Office Action of U.S. Appl. No. 11/768,167 mailed Dec. 27, 2010.
Notice of Abandonment of U.S. Appl. No. 11/620,046 Mailed Jan. 21, 2011.
Dugan, U.S. Appl. No. 12/979,275, filed Dec. 27, 2010.
Final Office Action of U.S. Appl. No. 11/768,167 mailed Aug. 19, 2011.
Notice of Abandonment of U.S. Appl. No. 10/094,396 mailed Oct. 21, 2011.
Office Action of U.S. Appl. No. 12/538,862 mailed Nov. 17, 2011.
Office Action of U.S. Appl. No. 12/426,193 mailed Jul. 27, 2012.
Ichinoseki-sekine et al., "Improving the Accuracy of Pedometer Used by the Elderly with the FFT Algorithm," Medicine & Science in Sports & Exercise 2006,1674-1681.
May 17, 2012 Response to Office Action of U.S. Appl. No. 12/538,862.
Final Office Action of U.S. Appl. No. 12/538,862 mailed Jul. 31, 2012.
Appeal Brief of U.S. Appl. No. 10/094,396 filed Dec. 14, 2009.
Reply Brief of U.S. Appl. No. 11/692,185 filed Nov. 22, 2010.
Restriction Requirement of U.S. Appl. No. 11/768,167 mailed Feb. 5, 2009.
Apr. 6, 2009 Response to Restriction Requirement of U.S. Appl. No. 11/768,167.
Feb. 21, 2012 Response to Final Office Action of U.S. Appl. No. 11/768,167.
Final Office Action of U.S. Appl. No. 11/768,167 mailed Sep. 7, 2012.
Mann, W. et al., "Smart Phones for the Elders: Boosting the Intelligence of Smart Homes," Am. Assoc. for Artificial Intell., (AAAI), Jul. 2002.
Office Action of U.S. Appl. No. 13/183,405 mailed Apr. 30, 2012.
Dugan, U.S. Appl. No. 13/433,285, filed Mar. 28, 2012.
Dugan, U.S. Appl. No. 13/440,987, filed Apr. 5, 2012.
Dugan, U.S. Appl. No. 13/456,196, filed Apr. 25, 2012.
Dugan, U.S. Appl. No. 13/488,436, filed Jun. 4, 2012.

* cited by examiner

SYSTEMS AND METHODS FOR PORTABLE EXERGAMING

CROSS REFERENCE TO RELATED APPLICATIONS

The present invention claims priority to U.S. Provisional Patent Application Ser. No. 61/226,624 filed Jul. 17, 2009 and entitled "SYSTEMS AND METHODS FOR PORTABLE EXERGAMING," which is hereby incorporated herein by reference in its entirety for all purposes.

The present application is related to the following co-pending U.S. patent applications, which are hereby incorporated herein by reference in their entirety for all purposes:

U.S. patent application Ser. No. 12/426,193, filed Apr. 17, 2009 and entitled "SYSTEMS AND METHODS FOR PROVIDING AUTHENTICATED BIOFEEDBACK INFORMATION TO A MOBILE DEVICE AND FOR USING SUCH INFORMATION"; and U.S. patent application Ser. No. 12/538,862, filed Aug. 10, 2009 and entitled "SYSTEMS AND METHODS FOR PROVIDING BIOFEEDBACK INFORMATION TO A CELLULAR TELEPHONE AND FOR USING SUCH INFORMATION".

FIELD OF THE INVENTION

The present invention relates to the use of biofeedback devices, and more particularly to systems and methods for portable exergaming.

BACKGROUND

Biofeedback devices such as portable heart rate monitoring (HRM) devices are commonly used in fitness related activities for weight loss, goal heart rate (HR) training, and general HR monitoring. Such devices may sometimes be employed by healthcare professionals for chronic and/or acute heart condition monitoring and/or diagnosis.

Portable HRMS and other monitoring devices typically are expensive, and in some cases are cost prohibitive for many consumers. A need exists for inexpensive and/or simplified monitoring systems.

SUMMARY OF THE INVENTION

In a some aspects of the invention, a system for playing a video game is provided that includes (1) one or more sensors adapted to monitor one or more biometric parameters of a user and communicate the one or more monitored biometric parameters (MBPs); (2) a computing device adapted to communicate with the one or more sensors and to receive the one or more communicated MBPs; and (3) a video game having an avatar adapted to move an object on an incline, the video game adapted to execute on the computing device. The video game is adapted to control the avatar to perform an action in the video game based in part on the received one or more communicated MBPs.

In some aspects of the invention, a video game is provided that is operable on a computing device that communicates with one or more sensors that monitor one or more biometric parameters of an exerciser. The video game includes an avatar adapted to move an object on an incline, the video game adapted to control the avatar to perform an action relating to moving the object on the incline based in part on one or more biometric parameters communicated from the one or more sensors to the computing device.

In some aspects of the invention, a method is provided that includes (1) providing a video game on a computing device, the video game having an avatar that moves an object on an incline; (2) employing the computing device to receive one or more biometric parameters of an exerciser; and (3) selecting an action relating to moving the object on the incline based in part on one or more biometric parameters received by the computing device. Numerous other aspects are provided.

Other objects, features and aspects of the present invention will become more fully apparent from the following detailed description of the preferred embodiments, the appended claims and the accompanying drawings.

DETAILED DESCRIPTION

Figure 1:
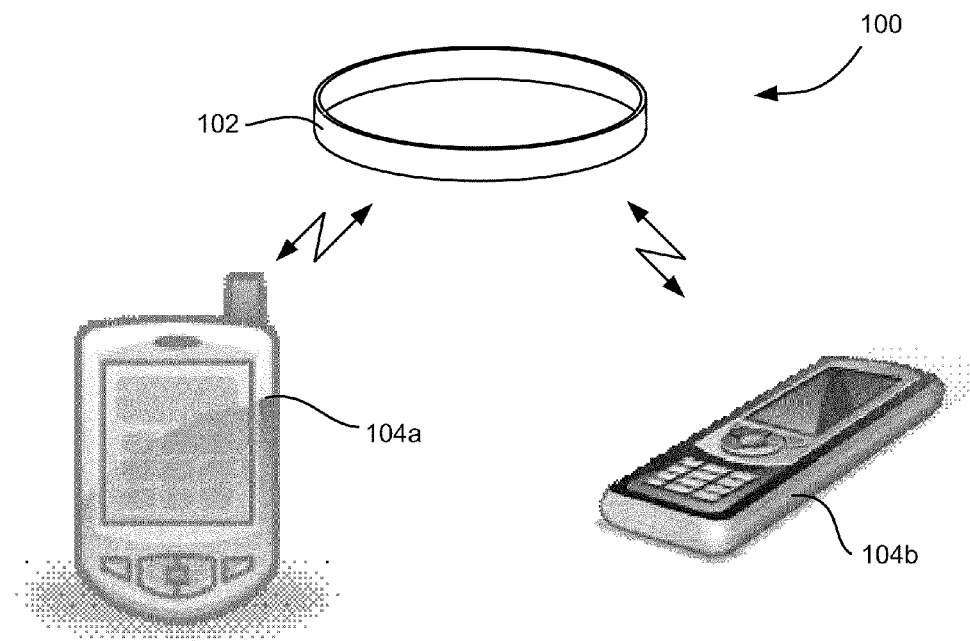
FIG. 1 is a schematic diagram of an exemplary system for sensing, collecting and/or monitoring biometric information from a user according to some embodiments of the present invention.

In one or more embodiments of the invention, wearable monitors and/or sensors are provided which may communicate wirelessly with a mobile device such as a cellular telephone, personal digital assistant (PDA) or other portable computing device. The monitor may be mounted on a user such that the monitor measures biometric information of the user. This information may be communicated to a portable computing device. Based on this information, the portable computing device may control and dynamically change a computer game to encourage exercise. The user may also directly control the game by controlling their biometrics.

In one example, a wrist, ankle, neck, thigh, back, head, hair, ear, eye, mouth, nose, finger, toe, or any other suitable body part/area band, strap, belt, bracelet, cover, shirt, pant, sock, glove, clip, or any other practicable securing mechanism may include one or more monitors or sensors adapted to sense biometric information from a user and to transmit this information to a cellular telephone, personal digital assistant or other portable device. Based on this information, the computing device may control aspects of a computer game. For instance, the user may control the actions of an avatar based on their biometric data.

If the user's biometric information is not within a predetermined range, the mobile computing device may modify the game play to encourage the user to keep their biometric data within the predetermined range. Exemplary biometric information that may be monitored includes, but is not limited to, heart rate, pulse rate, temperature, respiration, acceleration, skin resistivity, sweat, electrical impulses, positions of body parts (e.g., relative position of hands and feet), etc. Based on this information, a computing device can determine the type of exercise the user is performing, the length of time the user is performing the exercise, the level of fatigue of the user, etc.

In some embodiments, a retaining mechanism (e.g., a band or bracelet) may be provided at any suitable monitoring location, such as arms, legs or head of a user, to monitor movements and/or other biometrics of the user. In some embodiments, a retaining mechanism may be provided for each arm and/or each ankle of a user to monitor arm and/or leg position during exercise, golf, tennis, running, pushups, sit-ups, callisthenic exercise, weightlifting workouts (e.g., kettlebell workouts, etc.) etc. Such a system may be used, for example, to determine if the user has correct form during exercise, stride length during running, body position during a golf or tennis swing, "hang time" during a basketball dunk, and the like. In some embodiments, bands or bracelets may be provided for the torso, abdominals and/or the head of a user.

In some embodiments, a camera or other imaging device may be used with or without a band or bracelet to determine the biometric data and/or movements of a user. In some embodiments the imaging device may be mounted on the user and/or be part of the mobile computing device. In some embodiments, exercise equipment, such as a kettlebell, may be equipped with a monitor that may be used with or without an imaging device, band or a bracelet to determine biometric data of the user.

In one or more embodiments, an accelerometer may be provided within a retaining mechanism (e.g., a band or bracelet). The accelerometer may be employed to measure acceleration during a golf, tennis, hockey or other swing. Such acceleration information may be wirelessly transmitted to a computing device such as a cellular telephone, personal digital assistant or other portable device, and used to determine club, racquet or stick speed, club, racquet or stick velocity, swing tempo, or the like. In some embodiments, such acceleration information may be adjusted to compensate for the affects of gravity. In some embodiments, the accelerometer may be employed to measure acceleration during exercise, and the computing device may provide feedback to the user if the acceleration is within a range that may cause injury, or if the acceleration is outside of a predetermined range.

Software and/or one or more computer program products on the mobile computing device, such as a cellular telephone or other portable device, may be employed to calculate or otherwise determine any relevant information. A user can download the software using the internet, Bluetooth™, or any other suitable wireless protocol. A wireless or wired protocol may also be used to download software to the mobile computing device. The mobile computing device may store any information or software on a tangible, computer readable medium.

FIG. 1 is a schematic diagram of an exemplary system 100 for sensing, collecting and/or monitoring biometric information from a user (not shown). The example system 100 includes a wearable band 102 having one or more monitors or sensors (not shown) adapted to monitor or otherwise sense, for example, heart rate, pulse rate, temperature, respiration, acceleration, skin resistivity, or any other biometric information. The wearable band 102 may (wirelessly) transmit the biometric information to one or more cellular telephones 104a-b or other portable devices such as personal digital assistants, MP3 players, portable video game players, other portable computing devices, or the like. While two cellular telephones are shown in FIG. 1, it will be understood that any number of portable or mobile computing devices (e.g., 1, 2, 3, 4, 5, etc.), differing types of mobile computing devices, etc., may receive biometric information from the band 102.

Each cellular telephone 104a-b, or any other mobile computing device receiving information from the band 102, may be programmed to process the biometric information received from the band 102 (e.g., for general health monitoring, determining swing information, monitoring sleep patterns, enhancing video game performance by affecting a video game character or characteristic based on the biometric information, etc.).

In some embodiments, the band 102 may be flexible, continuous, sealed, adjustable, and/or water resistant.

Figure 2:
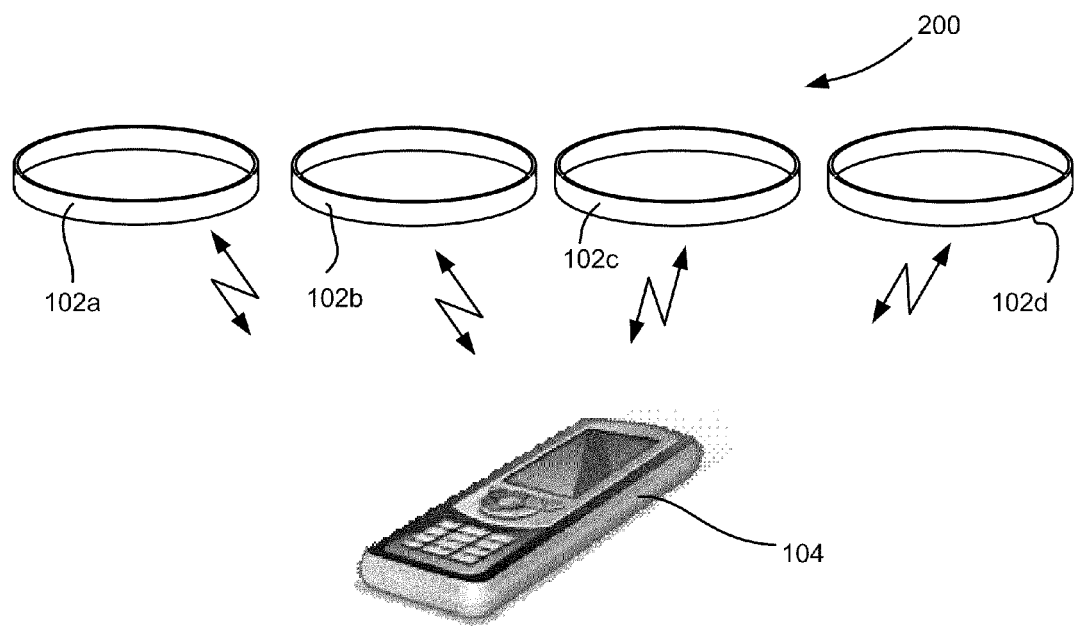
FIG. 2 is a schematic diagram of an alternative exemplary system for sensing, collecting and/or monitoring biometric information from a user according to some embodiments of the present invention.

FIG. 2 is a schematic diagram of an alternative system 200 for sensing, collecting and/or monitoring biometric information from a user (not shown). In the embodiment of FIG. 2, four bands 102a-d communicate information to a cellular telephone 104 (or other mobile computing device). For example, a user may employ a band 102 on each arm and each ankle, or multiple users may employ a band 102. Other numbers of bands and/or portable computing devices may be used.

Figure 3:
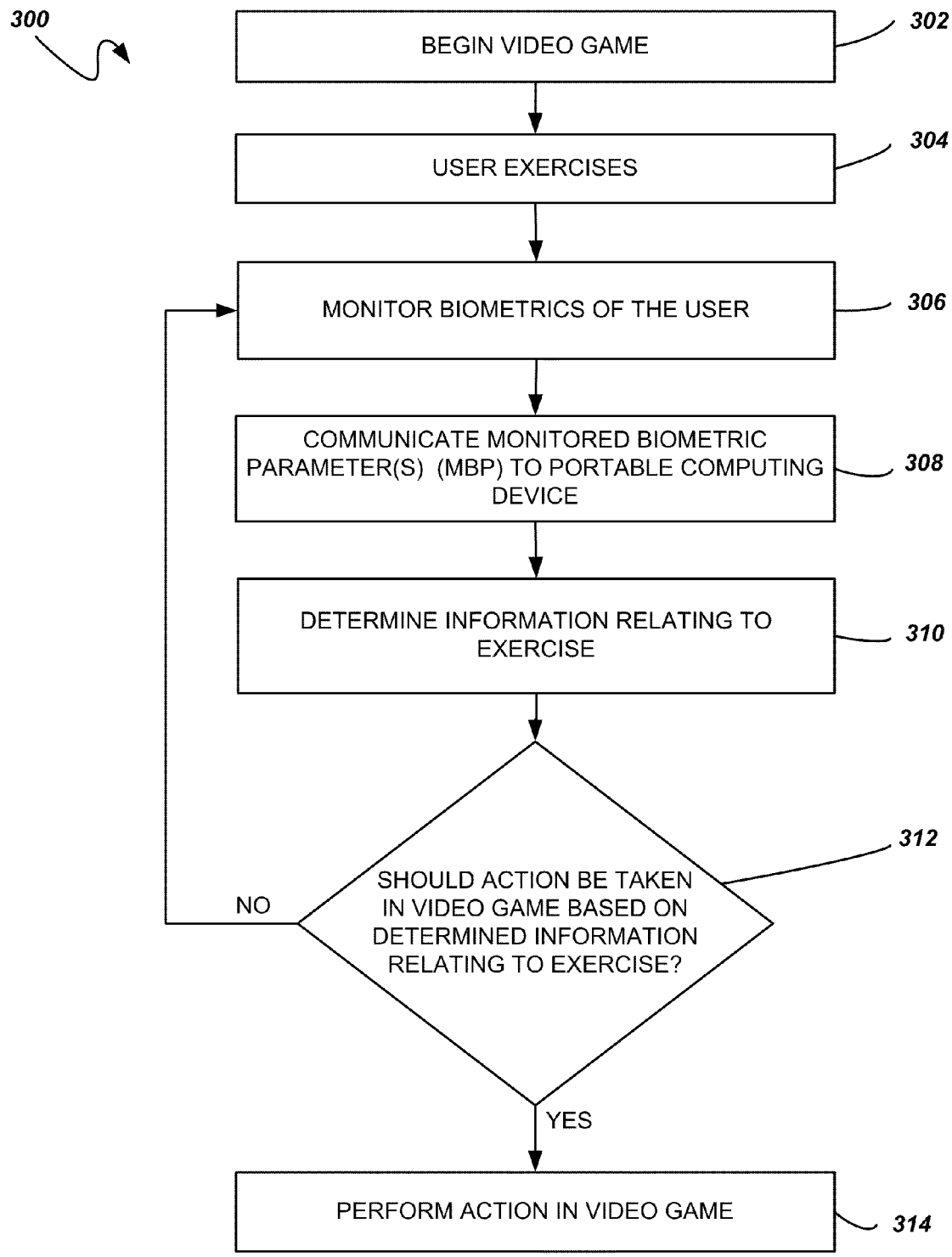
FIG. 3 is a flowchart illustrating an example method according to some embodiments of the present invention.

FIG. 3 illustrates an exemplary method 300 provided in accordance with the present invention. In step 302, the video game begins. The video game may include one or more aspects that are controlled by the user. The user may control the one or more aspects of the game based at least in part upon their biometrics. In some embodiments, the user may control the actions of an avatar or character in the game using the user's real world biometrics. In other words, by manipulating the user's own real world biometrics (e.g., heart rate), the user may directly control one or more parts/functions of the game and/or the user's avatar in the game.

In step 304, the user may exercise. By exercising, the user may control/manipulate and change his/her biometrics, and in turn control the avatar. As discussed above, biometric data may include heart rate, pulse rate, temperature, respiration, acceleration, skin resistivity, sweat, electrical impulses, position(s) of body parts (e.g., hands and/or feet), etc.

In step 306, one or more biometrics of the user are monitored by one or more sensors coupled to the user (e.g., one or more bands 102 of FIG. 1), exercise equipment, and/or a suitable imaging device.

In step 308, the monitored biometric(s), referred to herein as monitored biometric parameter(s) (MBP(s)) or just biometric parameters, are communicated to a mobile or portable computing device, such as a cell phone or PDA (e.g., cell phone 104a and/or 104b in FIG. 1). Each MBP may be communicated to the mobile computing device using a wired protocol or wireless protocol such as Bluetooth™ or via the internet.

In step 310, the mobile computing device may determine information relating to the exercise the user is performing (e.g., the type of the exercise the user is performing, duration of exercise, frequency of the exercise, etc.) based on the received MBP. The user may move differently during different exercises. If the user is wearing monitors on all four appendages, the relative motions and/or distances between appendages may be determined. For instance, during a pushup the user's hands and feet may remain mostly stationary, while during jumping jacks the users hands and feet move away from each other, and then towards each other. Based upon the relative motion and/or position of the appendages of the user, the mobile computing device may determine whether the user is performing jumping jacks or pushups. Thus, information relating to exercise may be determined by analyzing the relative positions and/or movements of the user's body parts. Of course, the computing device may also determine any number of other parameters such as heart rate, pulse rate, temperature, respiration, acceleration, skin resistivity, sweat, electrical impulses, etc.

In step 312, the computing device may determine if an action should be taken in the video game based upon the user's MBP. For instance, by performing a certain exercise (e.g., pushup, sit-up, jogging, pull-up, etc.), the avatar in the video game may perform an action (e.g., move up, down, left, right, etc.). In some embodiments, the user may be required to perform a certain amount of exercise, such as 10 pushups, before an action is performed in the video game. In some embodiments, the user must maintain his/her heart rate within a predetermined range or above/below a predetermined threshold before an action is performed in the game. In some embodiments, an exercise must be performed for a predetermined amount of time before an action is performed in the video game. If the computing device determines no action should be taken, the method returns to step 306 to repeat steps 306-312 (e.g., until the computing device determines an action should be taken in the video game, until a victory or fail condition is met in the video game, etc.). Note that some game actions may involve direct control of the avatar's actions (e.g., speed of the avatar, whether the avatar is standing or sitting, etc.) and some game actions may involve alteration of aspects of the game itself (e.g., the size of an object, the slope of an incline).

In step 314, if the computing device determines in step 312 that an action should be taken, the avatar performs an action in the video game (e.g., move the avatar, extend the life of the avatar, give the avatar additional powers, make the avatar larger and/or stronger, or otherwise allow the avatar to perform better in the game) or the game itself is otherwise altered.

Steps 302-314 may then repeat (e.g., until the user stops video game play and/or exercise).

Figure 4A:
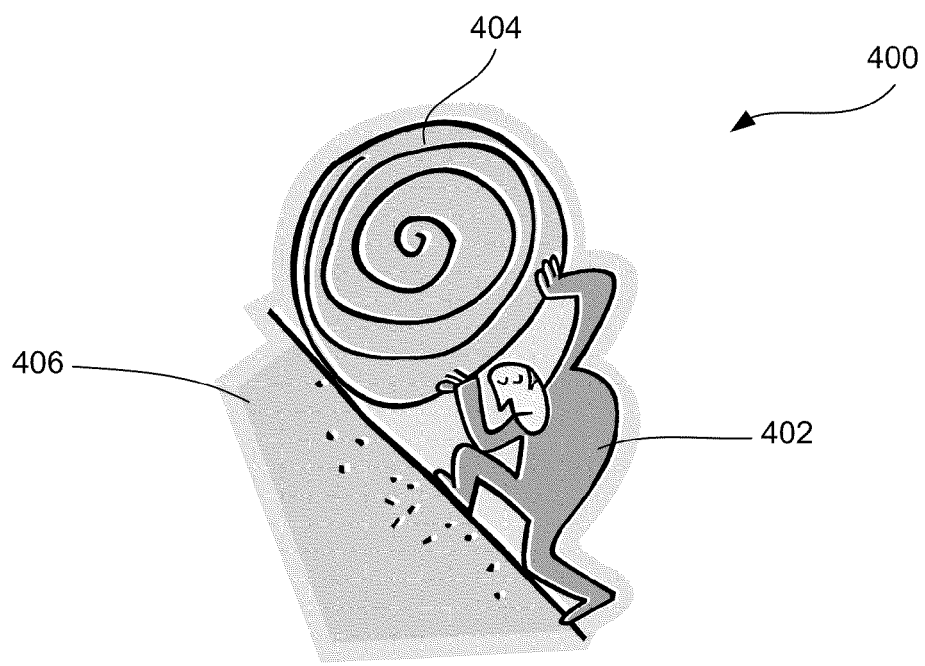
FIG. 4 illustrates a game that may implement some embodiments of the present invention.

In some embodiments of the invention, a video game is provided that motivates a user to exercise harder, more vigorously, longer, within a target range (e.g., within a defined heart rate or pulse-ox range), to achieve a fitness goal, to exercise more, faster, slower, or the like. The game is adapted to provide gaming entertainment to the user during exercise so that the user may be distracted from the work of the exercise. As illustrated in FIG. 4A, in one exemplary video game 400, called "Boulder Push" or "BP", an exerciser is provided with an avatar 402 that may or may not look like the exerciser. In some embodiments, the exerciser may customize the appearance of the avatar 402 (e.g., size, weight, clothing, gender, hair color, etc.). Further, exercise of the user may influence characteristics of the avatar (e.g., size, strength, stamina, etc.).

The video game 400 may start with the avatar 402 holding an object 404 (e.g., a boulder) on or near an incline 406 (e.g., a hill). One or more biometric parameters of the exerciser such as heart rate, pace, distance traveled, number of steps, etc., may be monitored (e.g., via a wrist band, chest strap, or the like, in communication with a game system such as a mobile computing device, cellphone, PDA, etc.). As the MBP of the exerciser changes, the avatar 402 may begin causing the object 404 to move up or down the incline 406. If the exerciser's MBP falls below a predetermined threshold, the movement of the object 404 up the incline 406, for example, may begin to slow down or reverse, for example. If the exerciser's MBP falls too low, the avatar 402 may lose control of the object 404 which may roll backward toward and/or crush the avatar 402. In some embodiments, if the exerciser's MBP falls above a predetermined threshold or outside a target range, the object 404 may slow down, stop rolling and/or begin to roll down the incline 406. In some embodiments, if the MBP falls above a predetermined threshold, the avatar 402 may reflect the fatigue of the exerciser by slowing down and/or by visually sweating or panting. In this manner, the exerciser is motivated to maintain his/her MBP within a desired range or to follow a defined pattern. A message (not shown) may flash on the video game screen and/or be audibly presented advising the exerciser to speed up, slow down or otherwise alter his/her exercise. The MBP also may be displayed along with an indication of the target range or predefined threshold required by the game.

In some embodiments, video game play or aspects of the game itself may dynamically change such that the slope/terrain of the incline 406 and/or the size/shape/type of the object 404 may change and may even be adjustable by the exerciser (e.g., by touching an input device such as a cellular phone running the video game, based on user heart rate or another biometric parameter, etc.). For instance, if the MBP is outside of a given range, the object 404 may increase in size or the incline 406 may become steeper. Sounds generated by the mobile computing device may be used to indicate the changes or other aspects of the game.

In some embodiments, the exerciser may design the characteristics of the incline 406 prior to or during exercise. In some embodiments, predefined incline 406 patterns may be selected that correspond to particular fitness or other goals. At the end or at some other milestone during an exercise routine, the avatar 402 may reach a summit of the incline 406, or roll the object 404 into one or more valleys. In some embodiments, the object 404 may roll down the other side of the incline 406 and crush a target such as trees, cars, a town, another player, or the like. In some embodiments, the object 404 may, for example, plug a crater of a volcano that is about to erupt (e.g., and failure to plug the crater within a predetermined time period may cause the demise of the avatar and/or other elements of the video game).

In some embodiments, the video game 400 may contain several challenges to motivate the exerciser to exercise. For instance, the characteristics of the incline 406 may change so that the exerciser has to control the avatar 402 to move the object 404 to the sides of the incline 406 (e.g., left or right) and/or let the object 404 move downhill to avoid obstacles, such as dead ends along a path or rocks that block the path of the avatar 402. Thus, the exerciser may control the avatar 402 to perform several different actions such as pushing the object 404 to the left, pushing the object 404 to the right, pushing the object 404 uphill, allowing the object 404 to move downhill, picking up the object 404, throwing the object 404, smashing the object 404 into smaller pieces, etc.

The exerciser may need to perform different physical exercises in the real world to control the avatar 402 to perform different actions in the game world. For instance, the exerciser may need to jog or run in the real world to cause the avatar 402 to push the object 404 up the incline 406 in the game, but perform pushups to push the object 404 to the left, perform sit-ups to move the object 404 to the right and perform jumping jacks to move the object 404 downhill. In some embodiments, the exerciser's MBP must stay within a desired range for a predetermined amount of time, such as 10 seconds, before an action, such as pushing the object 404, is performed.

The actions of the avatar may be controlled through any suitable MBP. In some embodiments, if the exerciser's heart rate is within a predetermined range, the avatar may perform a specific action. Several ranges may be selected so that different heart rates correspond to different actions the avatar may perform.

By having different exercises control different aspects of the video game 400, the exerciser may be encouraged to have a well balanced work out. For instance, the exerciser may exercise several muscle groups (e.g., pectorals, triceps, quadriceps, abdominals, biceps, etc.) and also use cardiovascular exercise to complete the video game.

In this manner a exerciser may have to complete one or more "circuits" to finish the video game or complete a level/portion of the video game. A circuit may be a combination of high-intensity aerobics and resistance training, for example. In some embodiments, a circuit is designed to be easy to follow and target fat loss, muscle building and/or heart fitness. An exercise circuit is one completion of all prescribed exercises. When one circuit is complete, the exerciser may stop exercising, begin the first exercise again for another circuit or start an entirely different exercise routine or circuit. In some embodiments, the time between exercises in circuit training may be short, often with rapid movement to the next exercise. An exemplary circuit may include:

1. Arms—pull-up or push-up
2. Abs—sit ups
3. Legs—step ups
4. Arms—shoulder press
5. Abs—sit-ups or plank exercises
6. Legs—burpees A burpee is a full body exercise used in strength training and as aerobic exercise. It is performed in several steps and starts from a standing position: 1) the user drops into a squat position with their hands on the floor in front of them, 2) the user kicks their feet back, while simultaneously lowering themselves into a pushup 3) the user immediately returns their feet to the squat position, while simultaneously pushing up with their arms and 4) the user leaps up as high as possible from the squat position with their arms overhead. In some embodiments, more or fewer exercises may be used in a circuit. For instance, a user may be required to jog between different exercises.

As discussed above, the exerciser may be required to complete one or more circuits to finish the video game 400. Each exercise of the circuit may correspond to a different action of the avatar 402. For instance, sit-ups may correspond to pushing the object 404 uphill, while push-ups may correspond to pushing the object 404 to the left and so forth. The exerciser may be presented with several challenges or obstacles that require the avatar 402 to perform different actions, which in turn correspond to different exercises the exerciser must perform. Thus, the challenges or obstacles in the video game 400 may be selected such that the exerciser completes all of the exercises in a circuit, or several circuits, to finish the video game 400 or complete a level of the video game 400.

In some embodiments, the computing device used to execute the video game 400 may be portable and may be transported by the exerciser during exercise. Thus, the exerciser may not necessarily be tied to a specific location during video game play. For instance, the exerciser may be required to do pushups at a first location, and then jog a predetermined distance away from the first location and arrive at a second location. The exerciser may then be required to perform another exercise at the second location and then jog another predetermined distance away and arrive at a third location. The exerciser may then perform another exercise at the third location. This may repeat until the game is completed. Accordingly, the exerciser is not tied to a specific location during game play. For instance, a exerciser may play the video game 400 outside of his/her home at any number of locations (e.g., park, track, gym, etc.), and transport the computing device during exercise.

Figure 4B:
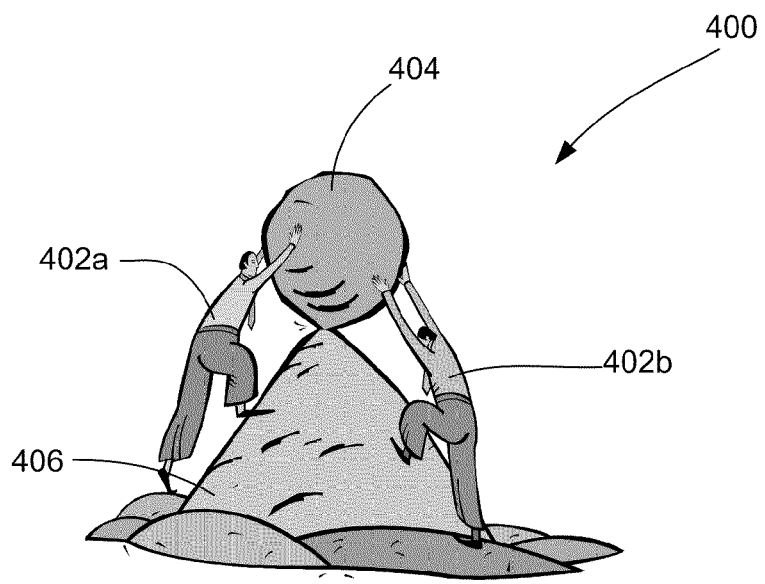

Multiplayer embodiments may be employed in which the avatars of players compete against one another or work together to move an object. For example, FIG. 4B illustrates a first avatar 402a and a second avatar 402b competitively rolling a single object 404 up and over a incline 406 at each other. In other embodiments, each avatar may roll a different object up the same (or a different) incline or toward another avatar or avatar's object (e.g., to block the other avatar's progress). Any number of players and/or avatars may be employed including multiple avatars for each user.

In some embodiments, different users can network their devices together via the internet. The users' computing devices may be connected to a server, or directly to each other. Any wired or wireless protocol may be used to connect the users' computing devices for multiplayer game play.

Any software discussed in this application may be implemented on a computing device or system, and saved onto a tangible, computer readable medium of the computing device or system.

In some embodiments, the object 404 may grow in size and/or weight as it rolls up the incline 406 (e.g., if the incline is snow covered). Alternatively, the object may erode or otherwise shrink in size and/or weight as it rolls up the incline 406.

While the present invention has been described primarily with regarding to video games operating on portable computing devices such as cellular telephones, PDAs, MP3 players, tablet computers, etc., it will be understood that other computing devices may be employed for similar exercise-controlled video game play such as desktop computers, non-portable video game players, etc.

Any methods or processes described herein may be implemented in software as a computer program product. Each computer program product may be carried by a medium readable by a computer (e.g., a carrier wave signal, a floppy disc, a hard drive, a random access memory, etc.).

Accordingly, while the present invention has been disclosed in connection with the exemplary embodiments thereof, it should be understood that other embodiments may fall within the spirit and scope of the invention, as defined by the following claims.

What is claimed is:

1. A system for playing a video game comprising:
one or more sensors adapted to monitor one or more biometric parameters of a user and communicate the one or more monitored biometric parameters (MBPs);
a computing device adapted to communicate with the one or more sensors and to receive the one or more communicated MBPs; and
a video game having an avatar adapted to move an object on an incline, the video game adapted to execute on the computing device,
wherein the video game is adapted to control the avatar to perform an action in the video game based in part on the received one or more communicated MBPs;
wherein the video game is adapted to control the avatar to perform a plurality of actions including moving the object up the incline, down the incline, to the left, or to the right; and
wherein the video game is adapted to select an action to perform from the plurality of actions based on the received one or more communicated MBPs.

2. The system of claim 1, wherein the video game is further adapted to:
determine a type of exercise the user is performing based in part upon the one or more communicated MBP; and
control the avatar to perform the action based in part upon the type of exercise the user is performing.

3. The system of claim 2, wherein the avatar is capable of performing a plurality of actions, and the video game is further adapted to control the avatar to perform one of the plurality of actions, based in part upon the type of exercise the user is performing.

4. The system of claim 1, wherein the video game is further adapted to:
   determine a duration of the exercise the user is performing; and
   control the avatar to perform the action based in part upon the duration of the exercise the user is performing.

5. The system of claim 1, wherein the video game is adapted such that to complete the video game, the user must perform one or more circuits of exercise.

6. The system of claim 1, wherein the computing device is adapted to be transported during execution of the video game.

7. A video game operable on a computing device that communicates with one or more sensors that monitor one or more biometric parameters of an exerciser, the video game comprising:
   an avatar adapted to move an object on an incline, the video game adapted to control the avatar to perform an action relating to moving the object on the incline based in part on one or more biometric parameters communicated from the one or more sensors to the computing device;
   wherein the video game is adapted to control the avatar to perform a plurality of actions including moving the object up the incline, down the incline, to the left, or to the right; and
   wherein the video game is adapted to select an action to perform from the plurality of actions based on one or more biometric parameters communicated from the one or more sensors to the computing device.

8. The video game of claim 7, wherein the video game is further adapted to:
   determine a type of exercise the user is performing based in part upon the one or more communicated biometric parameter; and
   control the avatar to perform the action based in part upon the type of exercise the user is performing.

9. The video game of claim 7, wherein the video game is further adapted to:
   determine a duration of the exercise the user is performing; and
   control the avatar to perform the action based in part upon the duration of the exercise the user is performing.

10. The video game of claim 7, wherein the video game is adapted such that to complete the video game, the user must perform one or more circuits of exercise.

11. The video game of claim 7, wherein the computing device is adapted to be transported during execution of the video game.

12. A method comprising:
   providing a video game on a computing device, the video game having an avatar that moves an object on an incline;
   employing the computing device to receive one or more biometric parameters of an exerciser; and
   selecting an action relating to moving the object on the incline based in part on one or more biometric parameters received by the computing device;
   wherein the video game is adapted to control the avatar to perform a plurality of actions including moving the object up the incline, down the incline, to the left, or to the right; and
   wherein the video game is adapted to select an action to perform from the plurality of actions based on one or more biometric parameters received by the computing device.

13. The method of claim 12, wherein the video game is further adapted to:
   determine a type of exercise the user is performing based in part upon the one or more communicated biometric parameter; and
   control the avatar to perform the action based in part upon the type of exercise the user is performing.

14. The method of claim 12, wherein the video game is further adapted to:
   determine a duration of the exercise the user is performing; and
   control the avatar to perform the action based in part upon the duration of the exercise the user is performing.

15. The method of claim 12, wherein the video game is adapted such that to complete the video game, the user must perform one or more circuits of exercise.

16. The method of claim 12, wherein the computing device is adapted to be transported during execution of the video game.

17. A system for playing a video game comprising:
   one or more sensors adapted to monitor one or more biometric parameters of a user and communicate the one or more monitored biometric parameters (MBPs);
   a computing device adapted to communicate with the one or more sensors and to receive the one or more communicated MBPs; and
   a video game having an avatar adapted to move an object on an incline, the video game adapted to execute on the computing device,
   wherein the video game is adapted to control the avatar to perform an action in the video game based in part on the received one or more communicated MBPs; and
   wherein the computing device is adapted to be transported during execution of the video game.

18. The system of claim 17, wherein the video game is further adapted to:
   determine a type of exercise the user is performing based in part upon the one or more communicated MBP; and
   control the avatar to perform the action based in part upon the type of exercise the user is performing.

19. The system of claim 17, wherein the video game is adapted such that to complete the video game, the user must perform one or more circuits of exercise.

20. A video game operable on a computing device that communicates with one or more sensors that monitor one or more biometric parameters of an exerciser, the video game comprising:
   an avatar adapted to move an object on an incline, the video game adapted to control the avatar to perform an action relating to moving the object on the incline based in part on one or more biometric parameters communicated from the one or more sensors to the computing device;
   wherein the computing device is adapted to be transported during execution of the video game;
   wherein the video game is further adapted to:
      determine a type of exercise the user is performing based in part upon the one or more communicated biometric parameter; and
      control the avatar to perform the action based in part upon the type of exercise the user is performing.

21. The video game of claim 20, wherein the video game is adapted such that to complete the video game, the user must perform one or more circuits of exercise.

22. A method comprising:
   providing a video game on a computing device, the video game having an avatar that moves an object on an incline;
   employing the computing device to receive one or more biometric parameters of an exerciser; and selecting an action relating to moving the object on the incline based in part on one or more biometric parameters received by the computing device;

wherein the computing device is adapted to be transported during execution of the video game;

wherein the video game is further adapted to:
   determine a type of exercise the user is performing based in part upon the one or more communicated biometric parameter; and
   control the avatar to perform the action based in part upon the type of exercise the user is performing.

23. The method of claim 22, wherein the video game is adapted such that to complete the video game, the user must perform one or more circuits of exercise.

* * * * *